US 11,666,648 B2

United States Patent
Jacobs, Jr. et al.

(10) Patent No.: US 11,666,648 B2
(45) Date of Patent: Jun. 6, 2023

(54) **DOUBLE AUXOTROPHIC *MYCOBACTERIUM* AND USES THEREOF**

(71) Applicant: Albert Einstein College of Medicine, Bronx, NY (US)

(72) Inventors: William R. Jacobs, Jr., Pelham, NY (US); Sangeeta Tiwari, Bronx, NY (US)

(73) Assignee: ALBERT EINSTEIN COLLEGE OF MEDICINE, Bronx, NY (US)

(*) Notice: Subject to any disclaimer, the term of this patent is extended or adjusted under 35 U.S.C. 154(b) by 0 days.

(21) Appl. No.: 17/268,789

(22) PCT Filed: Aug. 15, 2019

(86) PCT No.: PCT/US2019/046703
§ 371 (c)(1),
(2) Date: Feb. 16, 2021

(87) PCT Pub. No.: WO2020/037148
PCT Pub. Date: Feb. 20, 2020

(65) Prior Publication Data
US 2021/0170008 A1    Jun. 10, 2021

Related U.S. Application Data

(60) Provisional application No. 62/764,696, filed on Aug. 15, 2018.

(51) Int. Cl.
| | |
|---|---|
| *A61K 39/04* | (2006.01) |
| *A61P 37/04* | (2006.01) |
| *C12N 15/52* | (2006.01) |
| *C12Q 1/6897* | (2018.01) |
| *A61K 39/00* | (2006.01) |

(52) U.S. Cl.
CPC .............. *A61K 39/04* (2013.01); *A61P 37/04* (2018.01); *C12N 15/52* (2013.01); *C12Q 1/6897* (2013.01); *A61K 2039/522* (2013.01)

(58) Field of Classification Search
None
See application file for complete search history.

(56) References Cited

U.S. PATENT DOCUMENTS

2018/0155711 A1    6/2018    Anderson et al.

OTHER PUBLICATIONS

Gordhan et al. Infection and Immunity, vol. 70 No. 6 p. 3080-3084, Jun. 2002.*
Berney et al. PNAS. vol. 112 No. 32 10008-10013, 2015.*
Shin and Lee. Microbial Cell Factories, 13:166, pp. 1-11, 2014.*
Berney, et al, "Essential roles of methionine and S-adenosylmethionine in the autarkic lifestyle of *Mycobacterium tuberculosis*", PNAS, Aug. 11, 2015, vol. 112, No. 32 (pp. 10008-10013).
International Search Report dated Oct. 28, 2019; International Application No. PCT/US2019/046703; International Filing Date Aug. 19, 2019 (5 pgs).
Jain et al., "Specialized Transduction Designed for Precise High-Throughput Unmarked Deletions in *Mycobacterium tuberculosis*", mBio vol. 5, issue 3, e01245-14. doi: 10.1128/mBio.01245-14, pp. 1-9.
Marquez-Batalla, et al., "Disseminated infection due to *Mycobacterium bovis* after intravesical BCG instillation", World Journal of Clinical Cases, Jul. 16, 2014, vol. 2, Issue 7, pp. 301-303.
Minassian, et al., "A Human Challenge Model for *Mycobacterium tuberculosis* Using *Mycobacterium bovis* Bacille Calmette-Guerin", Journal of Infectious Diseases, 2012, vol. 205; April 1, pp. 1035-1042.
Morales, A., "BCG: A throwback from the stone age of vaccines opened the path for bladder cancer immunotherapy", The Canadian Journal of Urology, vol. 24, issue 3, Jun. 2017, pp. 8788-8793.
Serretta, V., "Although rate, severe complications following intravescial bacillus Calmette-Guerin treatment should not be overlooked!", Infectious Dieseses, vol. 47, issue 10, 7pp. 32-733 DOI: 10.3109/23744235.2015.1055795.
Thilothammal, et al., "Does BCG vaccine prevent tuberculous meningitis?", Archives of Disease in Childhood, 1996, vol. 74, pp. 144-147.
Tiwari, et al, "Arginine-deprivation-induced oxidative damage sterilizes *Mycobacterium tuberculosis*", PNAS, vol. 115, No. 39, Sep. 25, 2018, pp. 9779-9784.
Vilcheze, et al, "Rational Design of Biosafety Level 2-Approved, Multidrug-Resistant Strains of *Mycobacterium tuberculosis* through Nutrient Auxotrophy", mBIO, vol. 9, issue 3, pp. 1-12; 9:E00938-18.https://doi.org/10.1128/mBio.00938-18 (12 pgs).
Written Opinion dated Oct. 28, 2019; International Application No. PCT/US2019/046703; International Filing Date Aug. 19, 2019 (8 pgs).

* cited by examiner

*Primary Examiner* — Oluwatosin A Ogunbiyi
(74) *Attorney, Agent, or Firm* — Cantor Colburn LLP

(57) ABSTRACT

Provided are attenuated strains of *M. tuberculosis* and *M. bovis* BCG which are double auxotrophic mutants with genes knocked out in the biosynthetic pathways for arginine and methionine, and compositions and methods of use thereof.

22 Claims, 18 Drawing Sheets

FIG. 9

DOUBLE AUXOTROPHIC *MYCOBACTERIUM* AND USES THEREOF

CROSS-REFERENCE TO RELATED APPLICATIONS

This application is a National Stage application of PCT/US2019/046703, filed on Aug. 15, 2019, which claims priority to U.S. Provisional Application No. 62/764,696, filed on Aug. 15, 2018, both of which are incorporated by reference herein in their entirety.

STATEMENT OF GOVERNMENT SUPPORT

This invention was made with government support under grant numbers AI026170 awarded by the National Institutes of Health. The government has certain rights in the invention.

BACKGROUND OF THE INVENTION

Tuberculosis (TB), a disease that globally kills 1.7 million people each year, is a major health problem. The situation is further worsened by emergence of multi-drug resistant (MDR) strains, extensively drug resistant (XDR) strains, and HIV co-infections. The rise in resistant *Mycobacterium tuberculosis* (Mtb) strains and HIV co-infections demands new vaccines and/or drug treatments. The only available vaccine against TB is the *Bacillus* Calmette-Guérin (BCG) vaccine, however, the BCG vaccine provides limited protection against pulmonary tuberculosis in adults. Moreover, the BCG vaccine has variable efficacy against Mtb, depending on the geographical region. Additionally, the failure of TB vaccine candidate testing in clinical trials is an economic burden as the clinical trials are expensive and only a few candidates can be tested at one time. Additionally, there is no safe human TB challenge model available to evaluate the efficacy of vaccine candidates against TB.

The disclosures of all publications, patents, patent application publications and books referred to herein, are hereby incorporated by reference in their entirety into the subject application to more fully describe the art to which the subject invention pertains.

SUMMARY OF THE INVENTION

Provided is an auxotrophic *mycobacterium* comprising a mycobacterial genome in which (i) a gene encoding an enzyme essential in an arginine synthesis pathway has been fully or partially deleted and (ii) a gene encoding an enzyme essential in a methionine synthesis pathway has been fully or partially deleted.

Also provided is a composition comprising an auxotrophic *mycobacterium* with a mycobacterial genome in which (i) a gene (s) encoding an enzyme essential in an arginine synthesis pathway has been fully or partially deleted and (ii) a gene(s) encoding an enzyme essential in a methionine synthesis pathway has been fully or partially deleted, and a carrier.

Also provided is a method of eliciting an immune response in a subject comprising administering to the subject the composition or vaccine described herein in an amount effective to elicit an immune response.

Also provided is a method of vaccinating a subject comprising administering to the subject the composition or vaccine described herein in an amount effective to vaccinate a subject.

Also provided is a method of treating a subject for tuberculosis comprising administering to the subject the composition or vaccine described herein in an amount effective to treat a subject.

Also provided is a method of treating a subject for a cancer comprising administering to the subject the composition or vaccine described herein in an amount effective to treat a subject.

Also provided is a method of determining the efficacy of a candidate tuberculosis vaccine, comprising: administering the candidate tuberculosis vaccine to an animal which has been infected with the auxotrophic *mycobacterium* described herein, quantifying the amount of auxotrophic *mycobacterium* in the animal at one or more time points subsequent to administering the candidate tuberculosis vaccine, and comparing the amount of auxotrophic *mycobacterium* quantified to a predetermined control amount, or to the amount of auxotrophic *mycobacterium* infected into the animal, so as to determine the efficacy of the candidate tuberculosis vaccine.

Also provided is a method of determining the efficacy of a candidate small organic molecule tuberculosis treatment, comprising: administering the small organic molecule tuberculosis treatment to an animal which has been infected with the auxotrophic *mycobacterium* described herein, quantifying the amount of auxotrophic *mycobacterium* in the animal at one or more time points subsequent to administering the candidate tuberculosis vaccine, and comparing the amount of auxotrophic *mycobacterium* quantified to a predetermined control amount, or to the amount of auxotrophic *mycobacterium* infected into the animal, so as to determine the efficacy of the small organic molecule tuberculosis treatment.

BRIEF DESCRIPTION OF THE DRAWINGS

The above and other advantages and features of this disclosure will become more apparent by describing in further detail exemplary embodiments thereof with reference to the accompanying drawings.

Figure 1A:
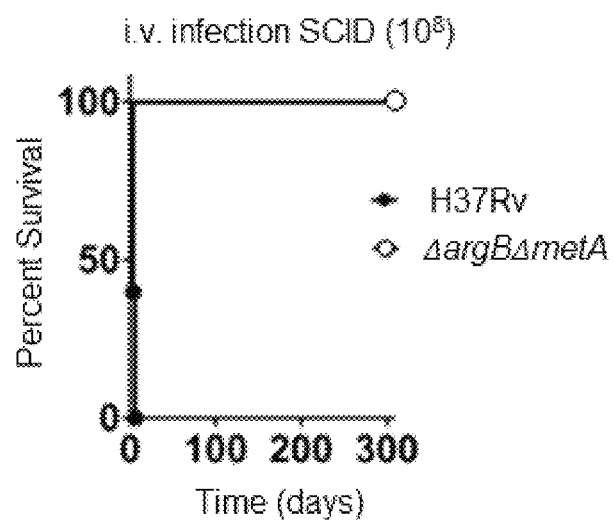
FIG. 1A is a graph of percent survival versus time (days) for severe combined immunodeficiency (SCID) mice intravenously infected with H37Rv (wild type (WT), virulent Mtb strain, black circles) or Mtb strain $\Delta argB\Delta metA$ (open circles), at a dose of $10^8$ bacilli/mice.
Figure 1B:
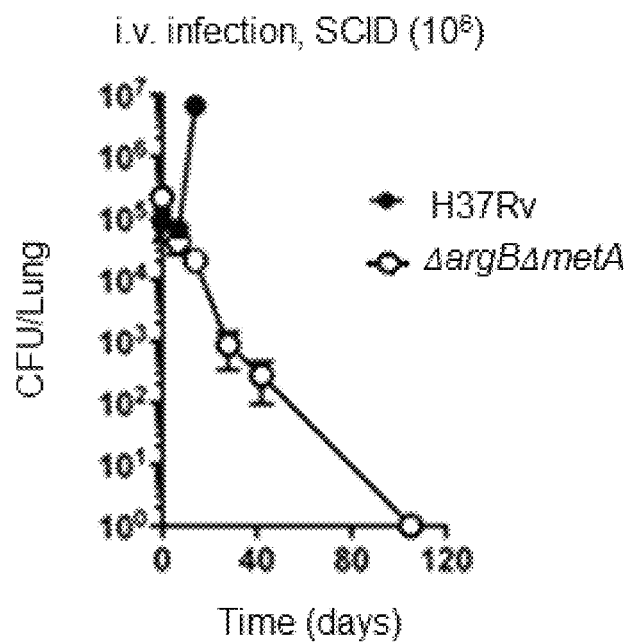
FIGS. 1B to 1D are graphs of colony forming units (CFU) per tissue versus time (days), showing the sterilization of Mtb strain $\Delta argB\Delta metA$ in the lung (FIG. 1B), liver (FIG. 1C), and spleen (FIG. 1D) of SCID mice infected by intravenous route with $10^6$ bacilli/mouse.
Figure 1C:
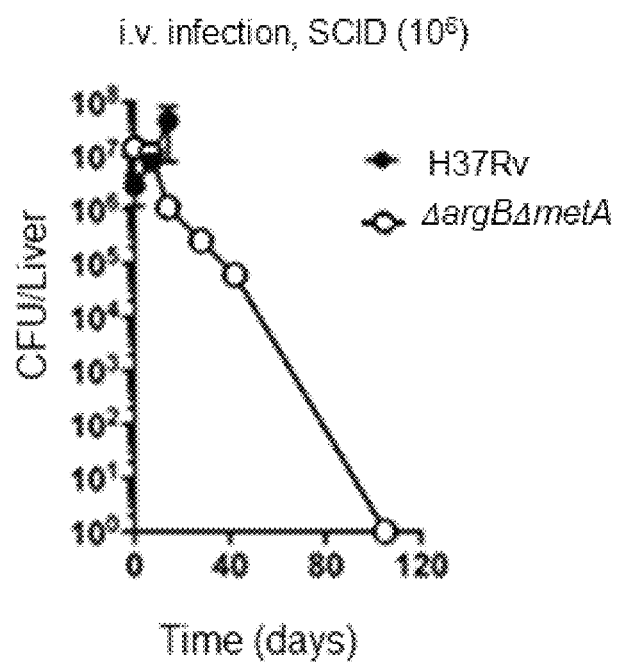
Figure 1D:
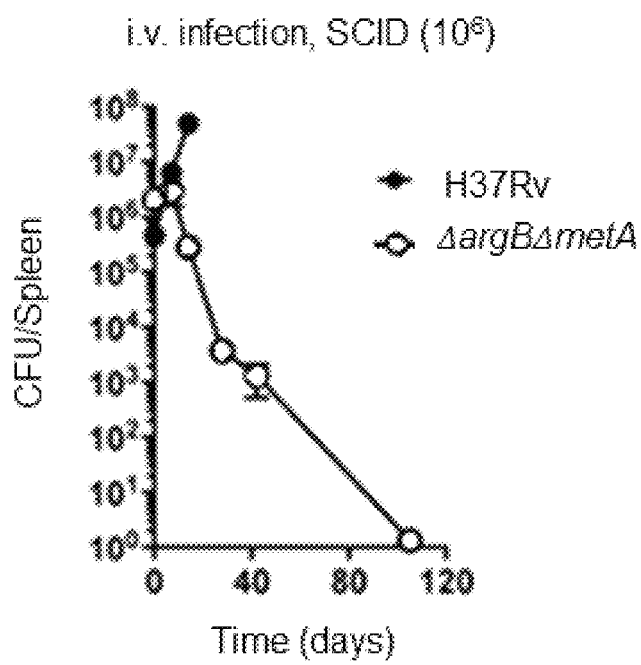
Figure 2A:
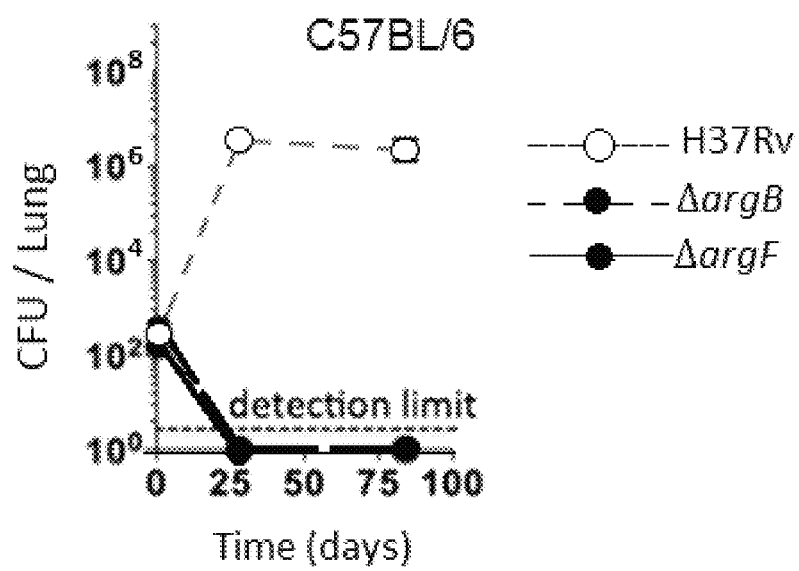
FIGS. 2A, 2B, and 2C are graphs of CFU/lung versus time (days) as detected in aerosol infected C57BL/6 mice (FIG. 2A), interferon gamma (IFN-$\gamma$) knock out mice (FIG. 2B) and inducible nitric oxide synthase (iNOS) knockout mice (FIG. 2C).
Figure 2B:
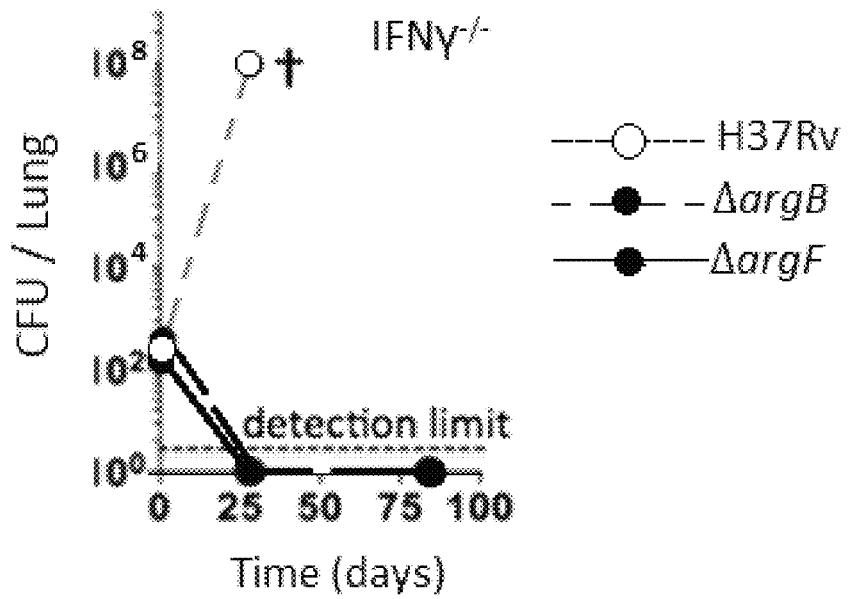
Figure 2C:
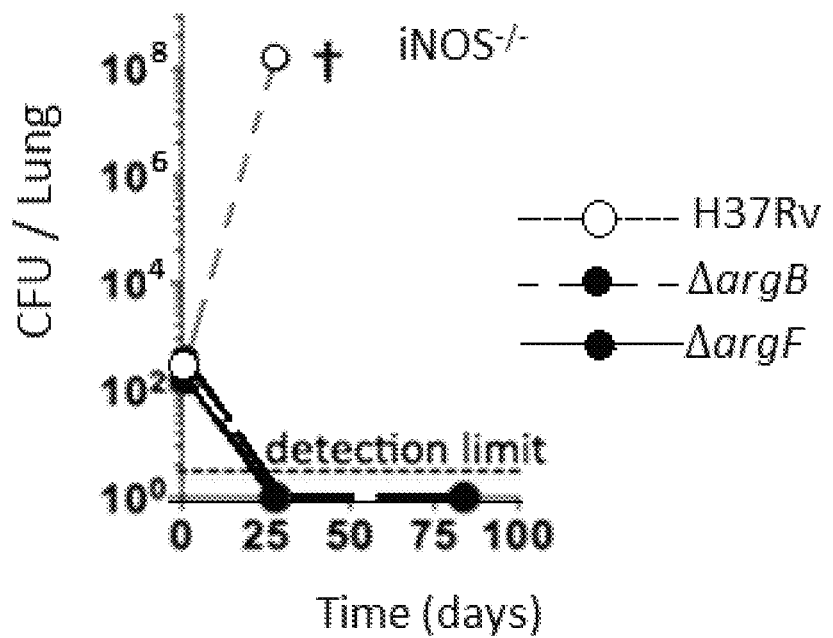
Figure 3:
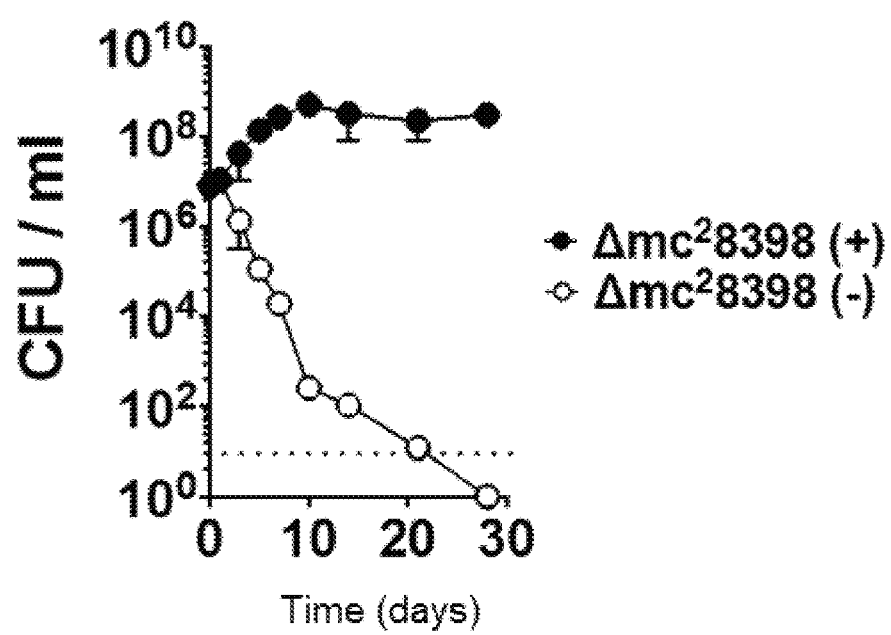
FIG. 3 is a graph of CFU/ml versus time (days) showing the growth of strain $mc^2 8398$ in arginine and methionine free media ($mc^2 8398^-$) and in arginine and methionine containing media ($mc^2\ 8398^+$).
Figure 4A:
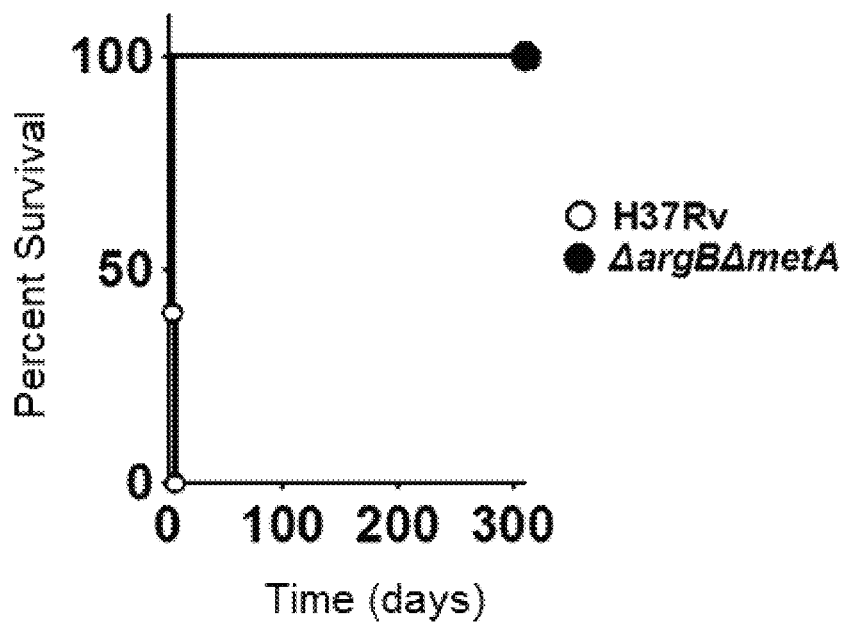
FIG. 4A is a graph of percent survival versus number of days showing the survival of strain $mc^2 8398$ in SCID mice.
Figure 4B:
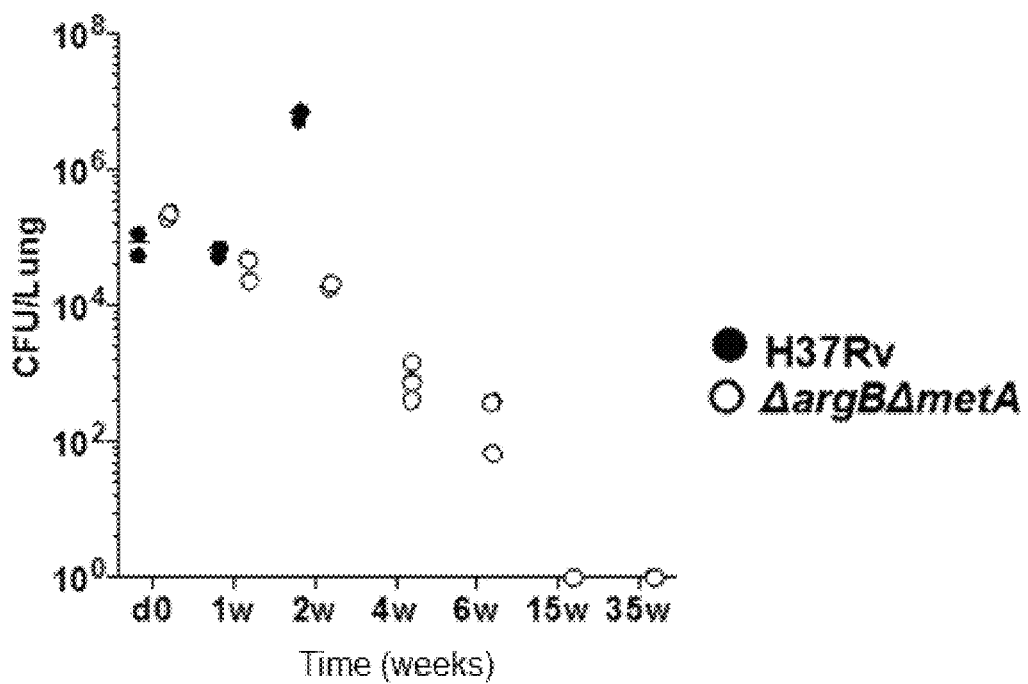
FIGS. 4B, 4C, and 4D are graphs of CFU per tissue versus time (weeks), showing the decrease in CFU over time in the lung (FIG. 4B), liver (FIG. 4C), and spleen (FIG. 4D) of SCID mice infected by the intravenous route with $10^6$ bacilli/mouse of strain $mc^2 8398$.
Figure 4C:
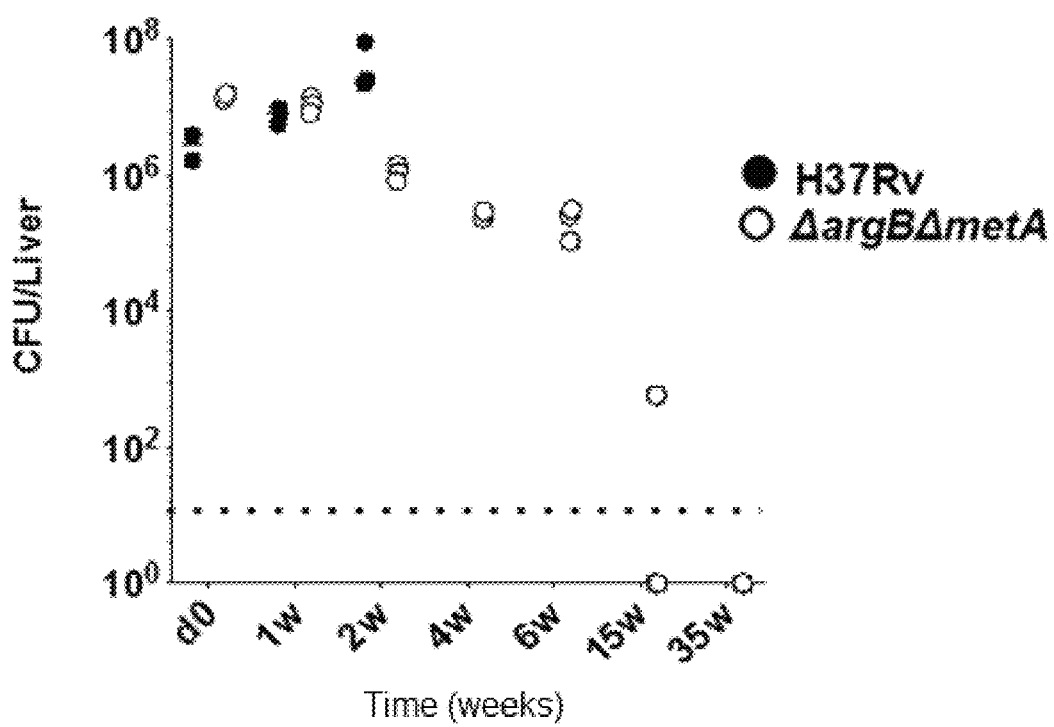
Figure 4D:
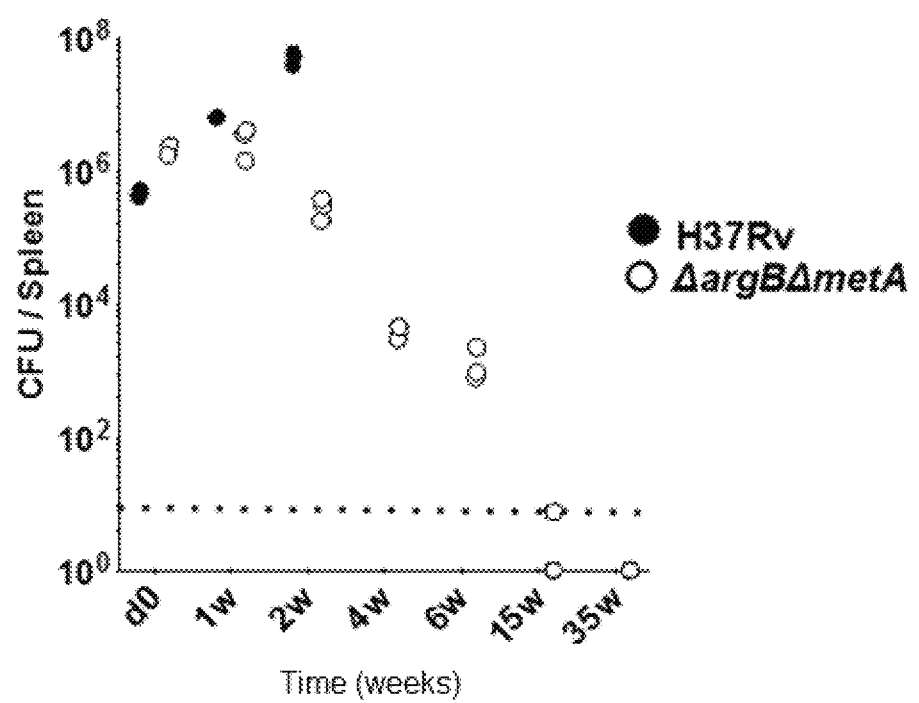
Figure 5A:
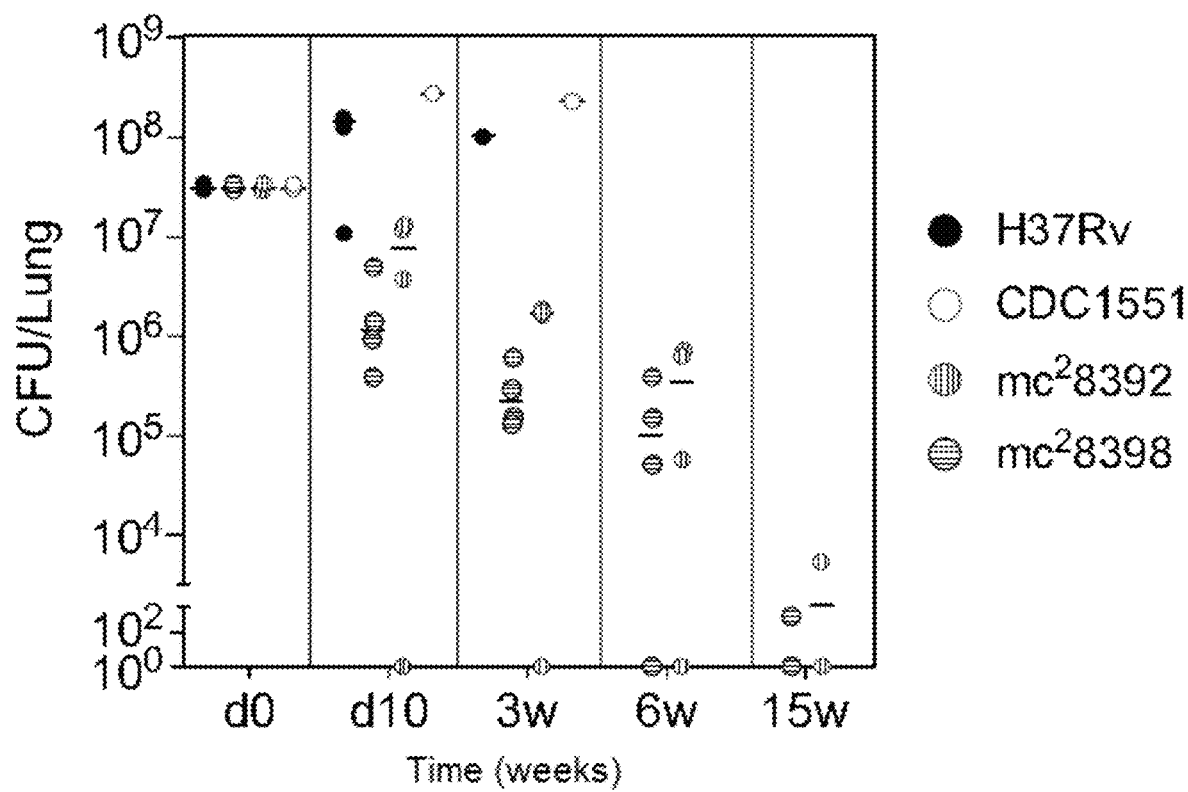
FIGS. 5A, 5B, and 5C are graphs of CFU per tissue versus time (weeks), showing the decrease in CFU over time in the lung (FIG. 5A), spleen (FIG. 5B), and liver (FIG. 5C) of immunocompromised $Rag^{-/-}$ mice infected by intravenous route with strains H37Rv, CDC1551, $mc^28392$, and $mc^28398$ at a dose of $10^6$ bacilli/mouse.
Figure 5B:
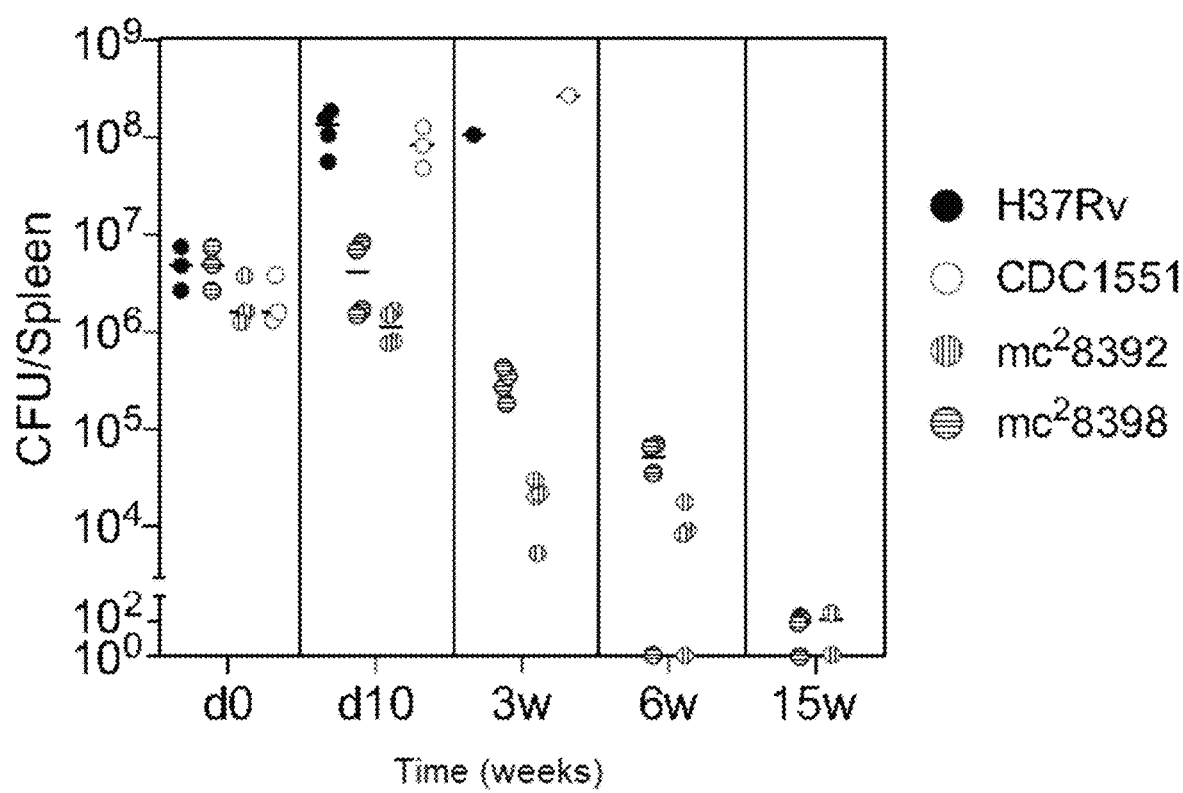
Figure 5C:
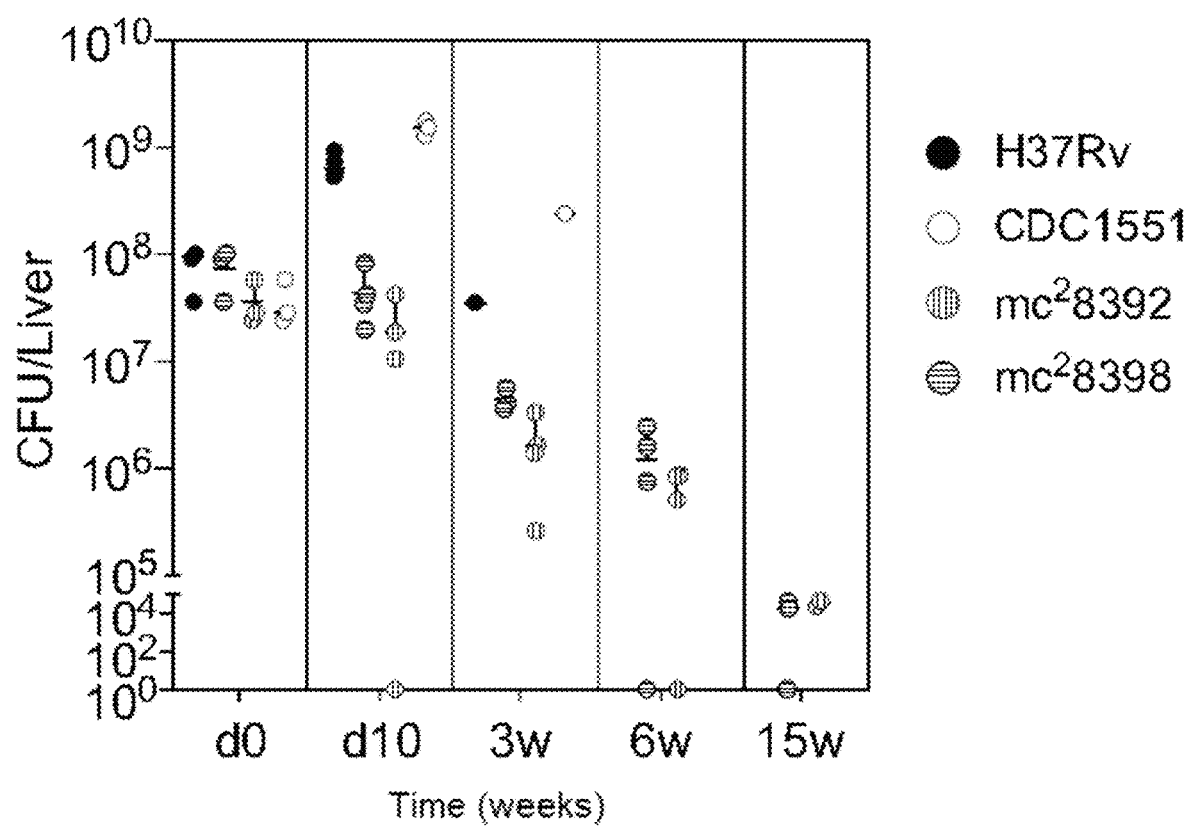
Figure 6A:
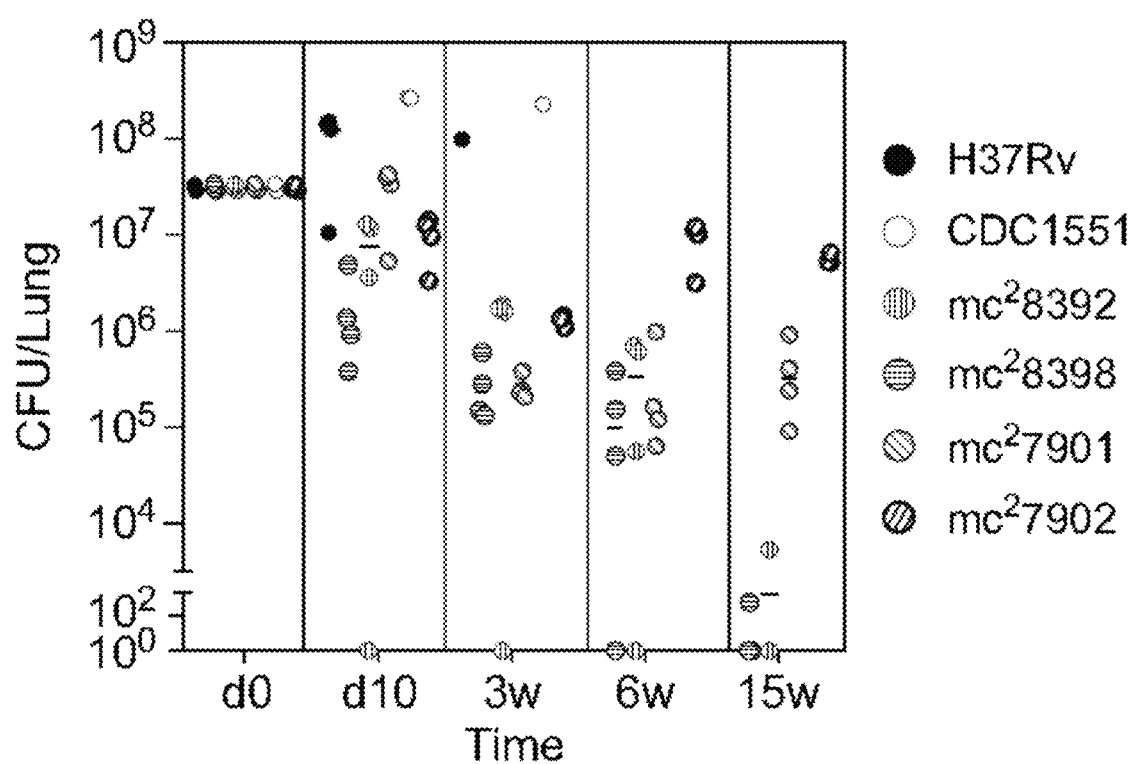
FIGS. 6A, 6B, and 6C are graphs of CFU per tissue versus time (weeks), showing the decrease in CFU over time in the lung (FIG. 5A), spleen (FIG. 5B), and liver (FIG. 5C) of immunocompromised $Rag^{-/-}$ mice infected by intravenous route with strains H37Rv, CDC1551, $mc^28392$, $mc^28398$, $mc^27901$, and $mc^27902$ at a dose of $10^6$ bacilli/mouse.
Figure 6B:
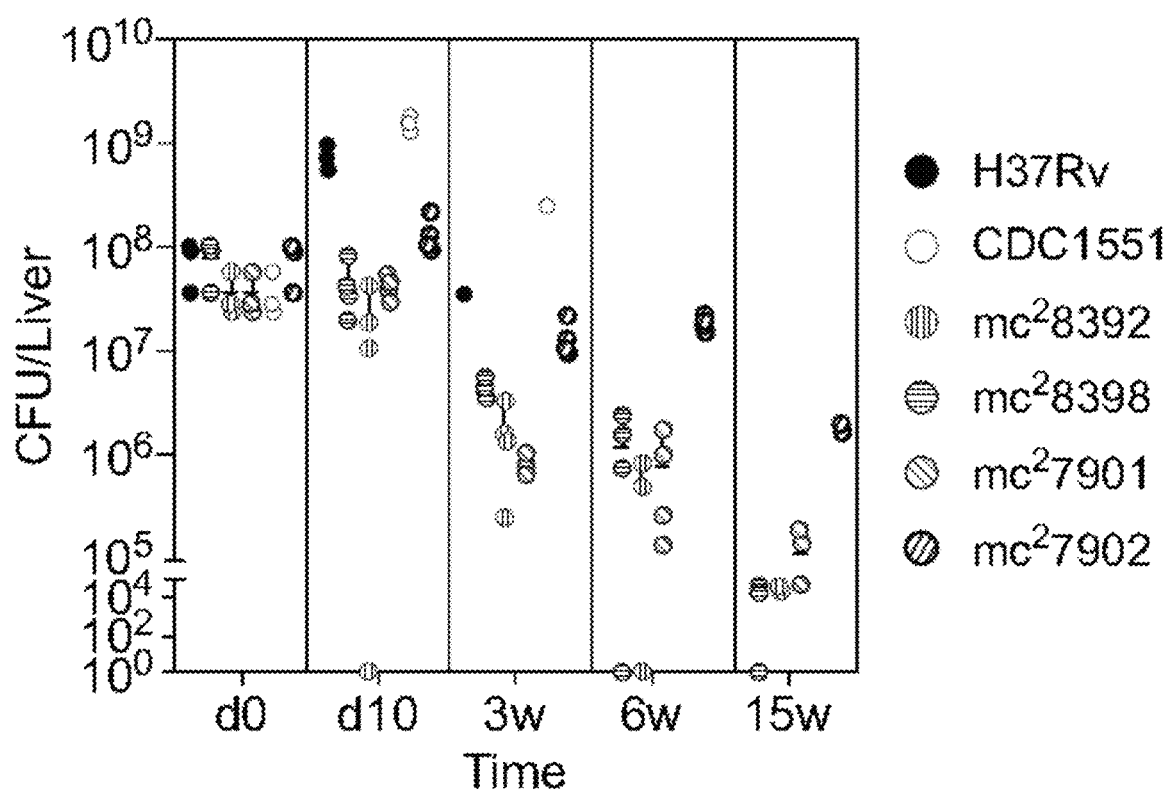
Figure 6C:
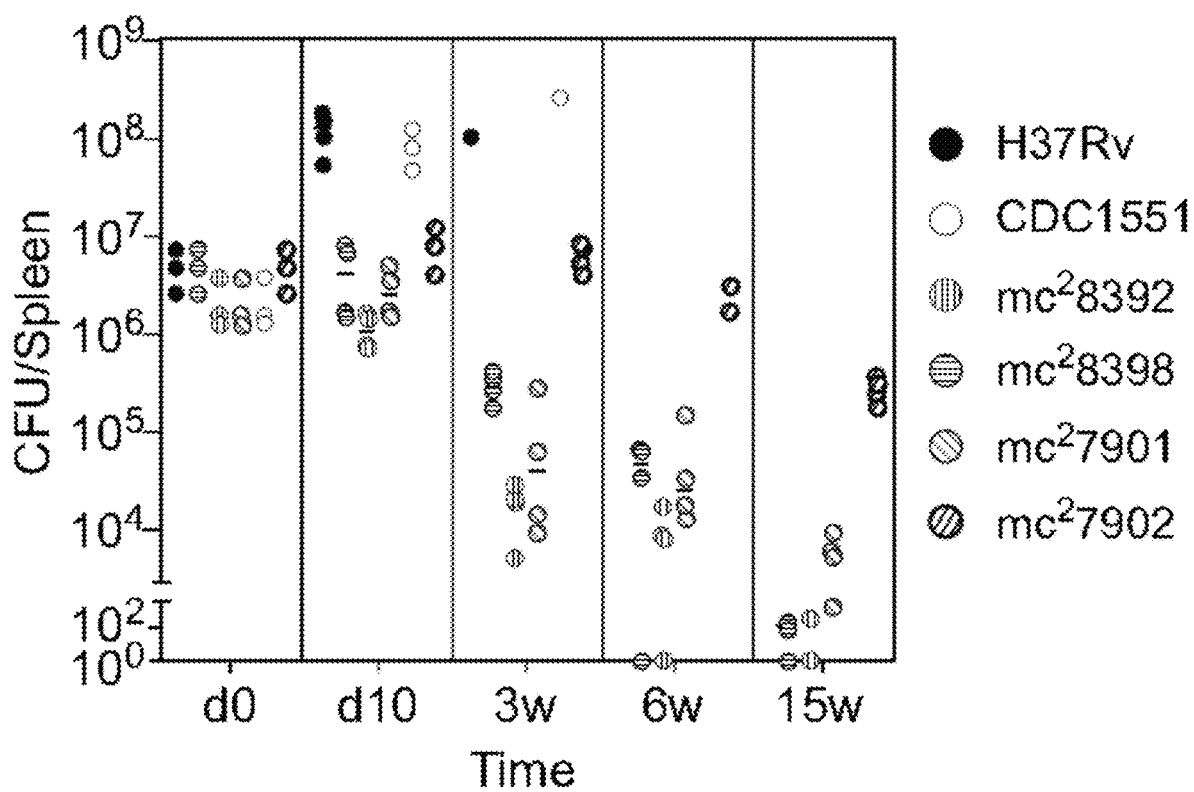
Figure 7:
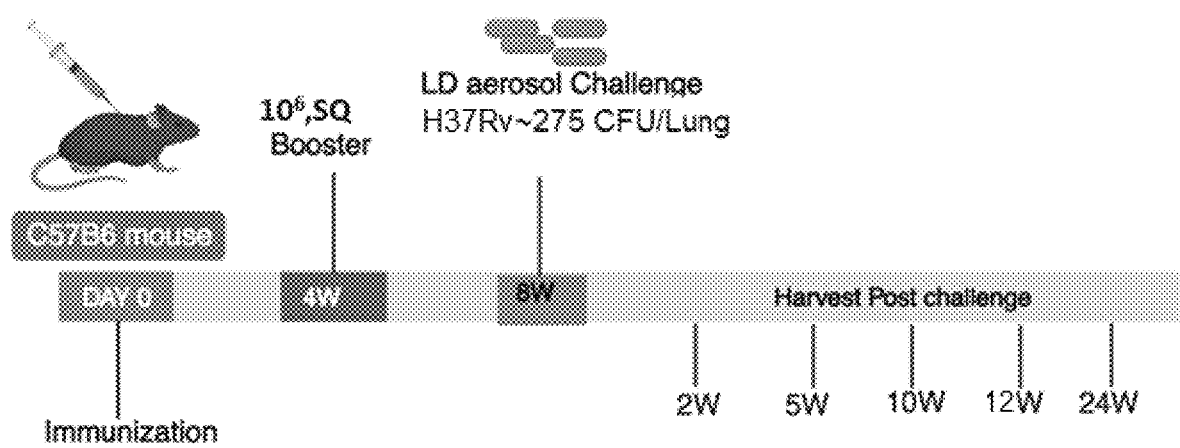
FIG. 7 is a diagram illustrating the immunization and challenge schedule of an experiment designed to evaluate the efficacy of strain $mc^28398$ to protect against challenge with wild type *Mycobacterium tuberculosis* strain H37Rv, by different routes of immunization.

FIG. 9 is a diagram illustrating the immunization and challenge schedule of an experiment designed to evaluate the efficacy of Mtb strain ΔargBΔmetA against wild type *Mycobacterium tuberculosis* strain H37Rv by different routes of immunization.

DETAILED DESCRIPTION

Provided is a *mycobacterium* comprising a mycobacterial genome in which (i) at least one gene encoding an enzyme essential in an arginine synthesis pathway has been fully or partially deleted and (ii) at least one gene encoding an enzyme essential in a methionine synthesis pathway has been fully or partially deleted. The *mycobacterium* is thus an auxotrophic *mycobacterium*, and more specifically, is a double deletion mutant that is auxotrophic for methionine and arginine.

In embodiments, the auxotrophic *mycobacterium* is incapable of synthesizing arginine and methionine.

In embodiments, the auxotrophic *mycobacterium* prior to the full or partial gene deletions of a gene encoding an enzyme essential in an arginine synthesis pathway and a gene encoding an enzyme essential in a methionine synthesis pathway is a *Mycobacterium tuberculosis.*

In embodiments, the auxotrophic *mycobacterium* prior to the full or partial gene deletions of a gene encoding an enzyme essential in an arginine synthesis pathway and a gene encoding an enzyme essential in a methionine synthesis pathway is a *Mycobacterium bovis Bacillus* Calmette-Guérin.

The auxotrophic *mycobacterium* can comprise a mycobacterial genome in which a single gene encoding an enzyme essential in an arginine synthesis pathway is fully or partially deleted from the mycobacterial genome or can comprise a mycobacterial genome in which more than one (e.g., 2, 3, 4, etc.) gene encoding an enzyme essential in an arginine synthesis pathway can be fully or partially deleted from the mycobacterial genome. Similarly, the auxotrophic *mycobacterium* can comprise a mycobacterial genome in which a single gene encoding an enzyme essential in an methionine synthesis pathway is fully or partially deleted from the mycobacterial genome or can comprise a mycobacterial genome in which more than one (e.g., 2, 3, 4, etc.) gene encoding an enzyme essential in an methionine synthesis pathway can be fully or partially deleted from the mycobacterial genome.

In embodiments, the gene encoding an enzyme essential in an arginine synthesis pathway comprises an argA gene, an argB gene, an argE gene, an argF gene, or a combination thereof, or is an equivalent to the *Mycobacterium tuberculosis* gene, i.e. a gene which encodes an ArgA, ArgB, argE, argF enzyme in another *Mycobacterium* strain. The argA gene is a gene encoding a mycobacterial amino acid acetyltransferase ArgA enzyme, the argB gene is a gene encoding a mycobacterial acetylglutamate kinase ArgB enzyme, the argE gene is a gene encoding a mycobacterial acetylornithine deacteylase ArgE enzyme, and the argF gene is a gene encoding a mycobacterial ornithine carbamoyltransferase ArgF enzyme. In embodiments, the gene encoding an enzyme essential in an arginine synthesis pathway is a gene encoding a mycobacterial acetylglutamate kinase ArgB enzyme. For example, the argB gene is a gene encoding UniProtKB—P9WQ01 (ARGB_MYCTU).

In embodiments, the gene encoding an enzyme essential in a methionine synthesis pathway is comprises a metA gene, a metC gene, a metD gene, a metE gene, and a metF gene, or a combination thereof, or is an equivalent to the *Mycobacterium tuberculosis* gene, i.e., a gene which encodes a MetA enzyme in another *Mycobacterium* strain. The metA gene is a gene encoding homoserine O-acetyltransferase MetA enzyme, the metC gene is a gene encoding a mycobacterial cystathionine β-lyase MetC enzyme, the metE gene is a gene encoding a mycobacterial cobalamin-independent methionine synthase MetE enzyme, and the metF gene is a gene encoding a mycobacterial methylenetetrahydrofolate reductase MetF enzyme. In embodiments, the gene encoding an enzyme essential in a methionine synthesis pathway is a metA gene encoding a mycobacterial homoserine O-acetyltransferase MetA enzyme. In embodiments, the gene encoding an enzyme essential in a methionine synthesis pathway is a *Mycobacterium tuberculosis* gene encoding a mycobacterial homoserine O-acetyltransferase MetA enzyme.

In embodiments, the auxotrophic *mycobacterium* comprises a mycobacterial genome in which at least one of an argA gene, an argB gene, an argE gene, an argF gene, or a combination thereof is fully or partially deleted and at least one of a metA gene, a metC gene, a metD gene, a metE gene, and a metF gene, or a combination thereof is fully or partially deleted.

In embodiments, the auxotrophic mycobacteria comprises a mycobacterial genome in which at least one gene encoding a homoserine O-acetyltransferase MetA enzyme and an acetylglutamate kinase ArgB enzyme are fully or partially deleted. That is, the auxotrophic mycobacteria has a full or partial deletion of at least one gene encoding a homoserine O-acetyltransferase MetA enzyme and a full or partial deletion of at least one gene encoding a acetylglutamate kinase ArgB enzyme.

In embodiments, the auxotrophic *mycobacterium* prior to the full or partial gene deletions of a gene encoding an enzyme essential in an arginine synthesis pathway and a gene encoding an enzyme essential in a methionine synthesis pathway is an H37Rv *Mycobacterium tuberculosis* strain. In an embodiment, the H37Rv *Mycobacterium tuberculosis* strain (i.e. a *mycobacterium* prior to deletion of the relevant genes) is deposited with the American Type Culture Collection (ATCC) as Accession No. ATCC27294. In embodiments, the auxotrophic mycobacterial genome prior to the full or partial gene deletions of a gene encoding an enzyme essential in an arginine synthesis pathway and a gene encoding an enzyme essential in a methionine synthesis pathway is a H37Rv *Mycobacterium tuberculosis* genome. In embodiments, the auxotrophic mycobacterial genome prior to the full or partial gene deletions of a gene encoding an enzyme essential in an arginine synthesis pathway and a gene encoding an enzyme essential in a methionine synthesis pathway is a H37Rv *Mycobacterium tuberculosis* Bacillus Calmette-Guérin. In an embodiment, the *Mycobacterium tuberculosis* Bacillus Calmette-Guérin (i.e. a *mycobacterium* prior to deletion of the relevant genes) is deposited with the ATCC as Accession No. ATCC 35737.

Also provided is a composition comprising an auxotrophic *mycobacterium* comprising a mycobacterial genome in which (i) a gene encoding an enzyme essential in an arginine synthesis pathway has been fully or partially deleted and (ii) a gene encoding an enzyme essential in a methionine synthesis pathway has been fully or partially deleted, and a carrier.

In embodiments, the composition is a vaccine. In embodiments, the composition further comprises an immunologic adjuvant.

To facilitate growth in vitro, the auxotrophic *mycobacterium* is grown in liquid or solid culture media which is supplemented with an amount of arginine and an amount of methionine. Accordingly, in embodiments, the composition comprises an amount of arginine, an amount of methionine, or a combination thereof. In embodiments, the composition comprises an amount of arginine and an amount of methionine.

In embodiments, the composition comprises an amount of arginine biosynthetic gene, an amount of methionine biosynthetic gene, or a combination thereof. In embodiments, the composition comprises an amount of the arginine biosynthetic gene and an amount of the methionine biosynthetic gene.

Optionally, the auxotrophic *mycobacterium* can be separated from the growth media and washed to remove residual traces of the media from the mycobacterial cells. Accordingly, in embodiments, the composition does not comprise arginine, methionine, or a combination thereof. For example, the composition does not comprise arginine, or the composition does not comprise methionine, or the composition does not comprise arginine and methionine.

In embodiments, the auxotrophic *mycobacterium* further comprises a reporter gene insertion in the mycobacterial genome thereof and wherein the amount of auxotrophic *mycobacterium* in the animal at one or more time points is quantified by quantifying a reporter signal. For example, a plasmid encoding a reporter gene can be used to insert the reporter gene in the mycobacterial genome of the auxotrophic *mycobacterium*. The reporter gene can be a gene encoding a protein which when expressed, can be used to detect the presence of the auxotrophic *mycobacterium* in vivo. Examples of the reporter gene include, but are not limited to, a luciferase gene (e.g., NanoLuc®), a green fluorescent protein (GFP) gene, a red fluorescent protein (RFP) gene, a near-infrared fluorescent protein (iRFP) gene, and a tyrosinase gene.

Also provided is a method of eliciting an immune response in a subject, the method comprising administering to the subject the composition or vaccine described herein in an amount effective to elicit an immune response.

Also provided is a method of vaccinating a subject comprising administering to the subject an amount of the composition or vaccine described herein in an amount effective to vaccinate a subject.

Also provided is a method of treating a subject for tuberculosis comprising administering to the subject the composition or vaccine described herein in an amount effective to treat a subject.

In embodiments, the subject has pulmonary tuberculosis.

In embodiments, the tuberculosis is pulmonary tuberculosis.

In embodiments, the subject has tuberculosis meningitis.

In embodiments, the tuberculosis is tuberculosis meningitis.

Also provided is a method of treating a subject for a cancer comprising administering to the subject the composition or vaccine described herein in an amount effective to treat a subject.

In embodiments, the cancer is a genitourinary cancer.

In embodiments, the cancer is a non-invasive bladder cancer.

In embodiments, the amount of the composition is administered into (e.g., directly into) the bladder of the subject via a catheter.

In embodiments, the subject is immunocompromised.

In embodiments of the methods, the subject is human.

In embodiments of the methods, the auxotrophic mycobacterial genome comprises no additional gene deletions.

Also provided is a method of determining the efficacy of a candidate tuberculosis vaccine, comprising: administering the candidate tuberculosis vaccine to an animal which has been infected with the auxotrophic *mycobacterium* described herein, quantifying the amount of auxotrophic *mycobacterium* in the animal at one or more time points subsequent to administering the candidate tuberculosis vaccine, and comparing the amount of auxotrophic *mycobacterium* quantified to a predetermined control amount, or to the amount of auxotrophic *mycobacterium* infected into the animal, so as to determine the efficacy of the candidate tuberculosis vaccine.

Also provided is a method of determining the efficacy of a candidate small organic molecule tuberculosis treatment, comprising: administering the small organic molecule tuberculosis treatment to an animal which has been infected with the auxotrophic *mycobacterium* described herein, quantifying the amount of auxotrophic *mycobacterium* in the animal at one or more time points subsequent to administering the candidate tuberculosis vaccine, and comparing the amount of auxotrophic *mycobacterium* to a predetermined control amount, or to the amount of auxotrophic *mycobacterium* infected into the animal, so as to determine the efficacy of the small organic molecule tuberculosis treatment.

In an embodiment of the carrier of the composition, the carrier is a pharmaceutically acceptable carrier.

In embodiments, the candidate small organic molecule tuberculosis treatment comprises a small organic molecule that is a potential candidate for treatment of disease caused by a MDR and/or XDR strain of *Mycobacterium tuberculosis*.

Examples of pharmaceutically acceptable carriers include, but are not limited to, phosphate buffered saline solution, sterile water (including water for injection USP), emulsions such as oil/water emulsion, and various types of wetting agents. Diluents for aerosol or parenteral administration include phosphate buffered saline or normal (0.9%) saline, for example 0.9% sodium chloride solution, USP. Compositions comprising such carriers are formulated by methods known to those of skill in the art (see, for example, Remington's Pharmaceutical Sciences, 18th edition, A. Gennaro, ed., Mack Publishing Co., Easton, Pa., 1990; and Remington, The Science and Practice of Pharmacy 20th Ed.

Mack Publishing, 2000, the content of each of which is hereby incorporated in its entirety). In non-limiting examples, the carrier can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate. A combination comprising at least one of the foregoing can also be used.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention may be better understood from the Experimental Details, which follow.

EXPERIMENTAL DETAILS

Herein disclosed is an auxotrophic *mycobacterium*, which is an auxotrophic *M. tuberculosis* (Mtb) strain and which can be used as a vaccine, as a treatment for TB, and which can also be safely used in a human TB challenge model. This auxotrophic *mycobacterium* Mtb strain represents a viable candidate for human challenge trials. Unlike BCG, or the leucine or pantothenate auxotrophic mutants of either BCG or *M. tuberculosis*, which persist in mammals, both the Mtb methionine auxotroph ΔmetA and the Mtb arginine auxotroph ΔargB are rapidly cleared in immunocompromised mice. In contrast, the ΔargBΔmetA double auxotroph is rapidly sterilized in media without arginine and/or methionine.

The auxotrophic *mycobacterium* strain with a reporter gene inserted therein, would give a functional human challenge test strain. Work with *M. tuberculosis* requires access to a BSL3 (biosafety level 3) facility, which is cumbersome and hazardous for large-scale drug screening programs. Herein is disclosed a safe, BSL2 (biosafety level 2) auxotrophic *mycobacterium* strain for screening drugs against *Mycobacterium tuberculosis* (Mtb). The auxotrophic *mycobacterium* strain has the same growth rate as wild type *M tuberculosis* strains when cultured in supplemented media. The auxotrophic *mycobacterium* strain does not persist and is sterilized in both in vitro and in vivo models. As shown in FIG. 1A, severe combined immunodeficient (SCID) mice infected with an extremely high dose of $10^8$ *mycobacterium*, were healthy and alive even at day 300-post infection, while mice infected with the parent strain (Mtb, strain H37Rv) were dead within 10 days. Additionally, no viable bacteria and no suppressor mutants that can bypass these deletions were recovered from the SCID mice.

Additionally, the auxotrophic *mycobacterium* strain can replace BCG to treat tuberculous meningitis and non-invasive bladder cancers. Several cases of BCG dissemination have been reported in BCG vaccinated people undergoing organ transplants or immunosuppressive treatments for cancer. BCG cannot be used in immunocompromised patients. BCG persists, is not sterilized in a SCID mouse model, and kills mice at later time points. Meanwhile, the auxotrophic *mycobacterium* strain disclosed herein has been demonstrated to be extremely safe.

Amino acid auxotrophies can be either bacteriostatic or bactericidal in vivo, but are not necessarily sterilizing. In Mtb most of the studied auxotrophies are bacteriostatic, however, the arginine and methionine amino acid auxotrophies described herein are sterilizing. As used herein, the terms "sterilization" and "sterilizing" refer to the death of the microorganism, which can occur either in vivo or in vitro. For example, the arginine or methionine deprived Mtb *bacillus* disclosed herein dies, i.e. does not persist, when deprived of arginine or methionine. Arginine or methionine deprivation rapidly sterilizes the auxotrophic *mycobacterium* strain having ΔargB or ΔmetA, which is deficient in the biosynthesis pathway of the respective amino acids, without the emergence of a suppressor mutant (i.e., a mutant that can bypass the deficiency in the pathway).

Testing of the Mtb strain ΔargB and the Mtb strain ΔmetA mutant for revertance during culture showed that the reversion rate is less than $1\times10^9$ cells for each mutation. Further, there is no emergence of a suppressor mutant either in vitro or in vivo in immunocompetent as well as in immunodeficient SCID mice. As shown in FIG. 1B, the auxotrophic Mtb strain ΔargBΔmetA is sterilized in the lung, liver, and spleen of SCID mice infected by the intravenous route with $10^6$ bacilli.

It was also found that auxotrophic Mtb strains deficient in de novo arginine biosynthesis pathway (ΔargB or ΔargF) are sterilized and do not persist in other tested immunodeficient ($INF\gamma^{-/-}$ and $phox^{-/-}$) mouse models. Mice were infected by aerosol with $10^6$ bacilli of Mtb ΔargB or Mtb ΔargF. (See FIGS. 2A-2C).

In summary, auxotrophic *mycobacterium* strains are extremely safe, non-persistent, and acquire no bypass mutations or suppressors in vitro and in vivo. As disclosed herein, the auxotrophic *mycobacterium* is a double auxotrophic strain having both arginine and methionine sterilizing auxotrophies combined in a single strain. Accordingly, the auxotrophic *mycobacterium* is safer and non-persistent.

Methods: Gene Knockout—The gene metA or argB can be deleted, in Mtb H37Rv and *M. bovis bacillus* Calmette-Guérin for example, by specialized transduction as described previously (Jain et al, *Specialized transduction designed for precise high-throughput unmarked deletions in Mycobacterium tuberculosis*. MBio 5 (3): e01245-e14). Transductants can be recovered on selective medium, e.g. containing hygromycin and methionine (50 μg/mL). Confirmation of transduction can be obtained by, e.g., by three-primer PCR using primers and Universal_uptag.

Table 1 shows various Mtb and *M. bovis* strains which have been constructed and/or tested.

TABLE 1

| | Strain no | Genotype | How Constructed |
|---|---|---|---|
| 1 | BCG SSI Danish | BCG SSI Danish | Jacobs Collection |
| 2 | $mc^28411$ | ΔmetA:: hyg sacB | Specialized transduction in BCG Danish using phAE783 |
| 3 | $mc^28412$ | ΔmetA | $mc^28411$ unmarked using phAE280 |
| 4 | $mc^28413$ | ΔmetA ΔargB:: hyg sacB | Specialized transduction in |

TABLE 1-continued

| | Strain no | Genotype | How Constructed |
|---|---|---|---|
| | | | me$^2$8412 with phAE773 |
| 5 | BCG Tice | BCG Tice | Jacobs Collection |
| 6 | mc$^2$8414 | ΔmetA:: hyg sacB | Specialized transduction with phAE783 in BCG Tice |
| 7 | mc$^2$2 | H37Rv | Jacobs Collection |
| 8 | mc$^2$7470 | ΔargB::hyg sacB | Specialized transduction of mc$^2$2 with phAE773 |
| 9 | mc$^2$7476 | ΔargB | mc$^2$7470 unmarked using phAE280 |
| 10 | mc$^2$8219 | ΔargB ΔmetA::hyg sacB | Specialized transduction of mc$^2$7476 with phAE773 |
| 11 | mc$^2$8398 | ΔargB ΔmetA | mc$^2$8219 unmarked using phAE280 |
| 12 | mc$^2$7680 | ΔargF::hyg sacB | Specialized transduction of mc$^2$2 with phAE774 |
| 13 | mc$^2$7958 | ΔargF | mc$^2$7680 unmarked using phAE280 |
| 14 | mc$^2$2600 | CDC1551 | Jacobs Collection |
| 15 | mc$^2$7477 | ΔargB::hyg sacB | Specialized transduction of CDC1551 using phAE773 |
| 16 | mc$^2$8211 | ΔargB | mc$^2$7477 unmarked using phAE280 |
| 17 | mc$^2$8392 | ΔargB ΔmetA::hyg sacB | Specialized transduction of mc$^2$8211 using phAE783 |
| 18 | mc$^2$7901 | ΔpanCD ΔleuCD ΔmetA | **Pantothenate-leucine-methionine (PLA) auxotroph; isoniazid resistant |
| 19 | mc$^2$7902 | ΔpanCD ΔleuCD ΔargB | **Pantothenate-leucine-arginine (PLA) auxotroph; rifampin resistant |

*Described in Tiwari, S. et al (2018) Arginine-deprivation-induced oxidative damage sterilizes *Mycobacterium tuberculosis*, Proc. Natl. Acad. Sci. USA, incorporated herein by reference.
**Described in Vilchèze, C, et al Rational Design of Biosafety Level 2-Approved, Multidrug Resistant Strains of *Mycobacterium tuberculosis* through Nutrient Auxotrophy, mBio, 9 (3): e00938-18, pages 1-12.

Figure 8A:
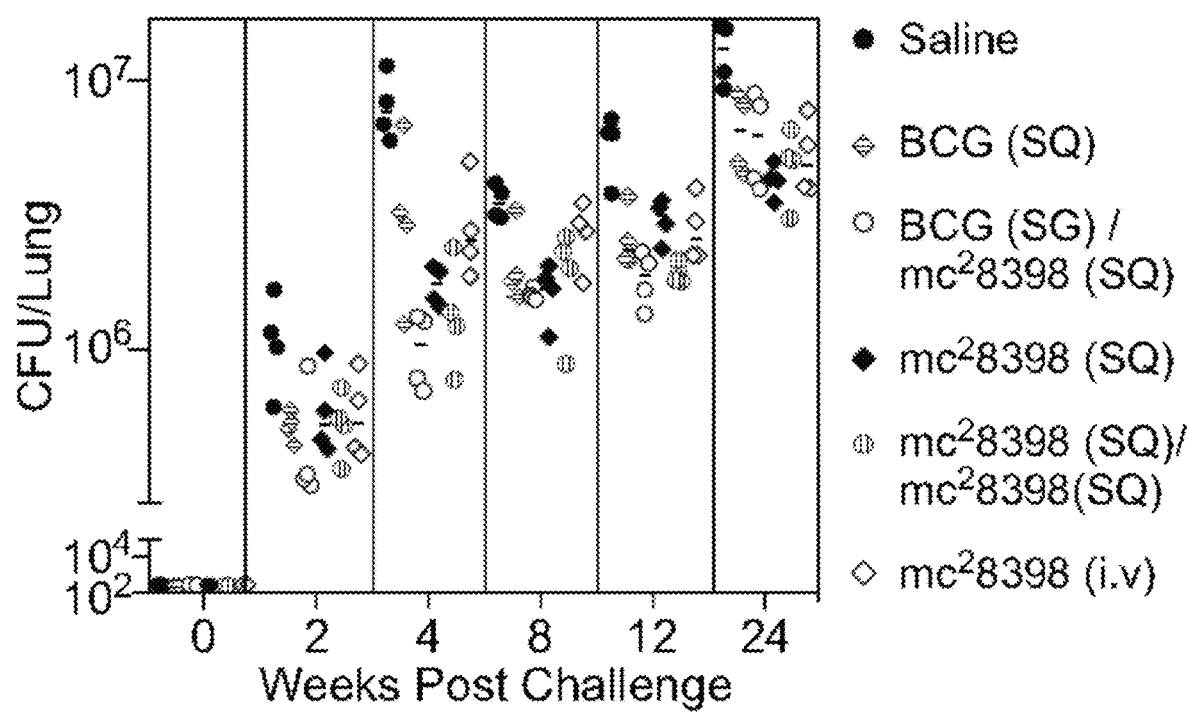
FIG. 8A is a graph of CFU per lung versus number of weeks post challenge with virulent *Mycobacterium tuberculosis* H37Rv and FIG. 8B is a graph of CFU per spleen versus number of weeks post challenge with virulent *Mycobacterium tuberculosis* H37Rv.
Figure 8B:
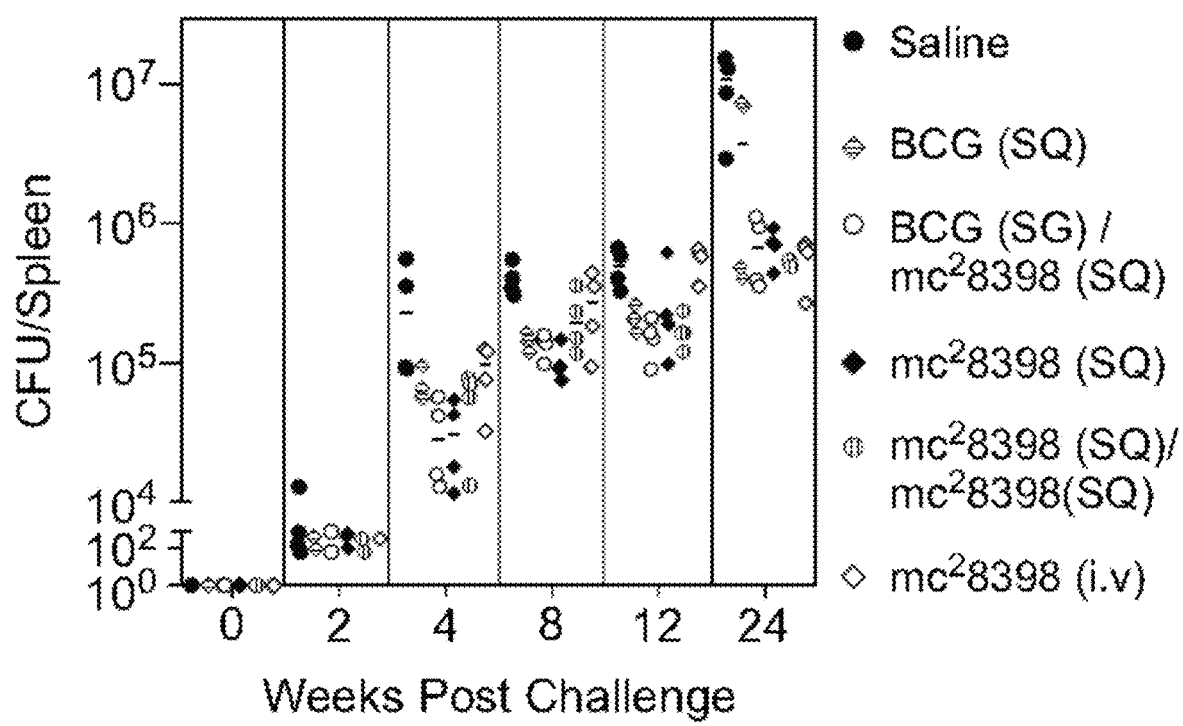

Deprivation of L-Arginine and L-Methionine Sterilizes *Mycobacterium tuberculosis.*

*Mycobacterium tuberculosis* strain mc$^2$8398 was cultured at 37° C. in Middlebrook 7H9 medium containing 10% OADC, 0.5% glycerol, and 0.05% tyloxapol, and further supplemented with L-arginine (1 mM) and L-methionine (50 μg/ml). Mid-log cultures were washed 5 times with PBS tyloxapol (PBST) and re-suspended in either arginine and methionine free media or arginine and methionine containing media (arginine 1 mM and L-methionine 50 μg/ml; mc$^2$8398$^+$). Samples were plated on arginine as well as methionine containing plates to determine CFU.

As shown in FIG. 3, the strain mc$^2$8398 grew well in arginine and methionine containing media (mc$^2$8398$^+$) whereas there was substantially no growth in the arginine and methionine free media (mc$^2$8398$^-$) and by 30 days, there was substantially no bacteria remaining.

Strain Mc$^2$8398 is Highly Attenuated in Immunocompromised SCID Mouse Model.

SCID mice (6/group) were infected with a high dose (10$^8$ bacilli/animal) of strain mc$^2$8398 or strain H37Rv. The percent survival of the mice over time is shown in FIG. 4A.

SCID mice (3/group) were infected with a high dose (10$^6$ bacilli/animal) of strain mc$^2$8398 or strain H37Rv, and the organ burden was determined by plating lung (FIG. 4B) Liver (FIG. 4C) and Spleen (FIG. 4D) on plates supplemented with both methionine and arginine.

The lung, liver, and spleen from infected mice, taken at different time points, were cultured on plates supplemented with arginine and methionine. As shown in FIGS. 4B to 4D, the Mtb ΔargBΔmetA was completely sterilized in the lung, liver, and spleen of the infected SCID mice by 120 days post-infection.

Strain Mc$^2$8398 is Attenuated in in Lung, Liver and Spleen of Rag$^{-/-}$ Mice Infected by Intravenous Route by 10$^8$ Bacilli/Mice.

In house bred Rag−/− mice were infected intravenously with WT (H37Rv, CDC1551) and auxotrophic strains (mc$^2$8392, mc$^2$8398) at a very high dose of 10$^8$ bacilli/animal. At the indicated time points, animals were sacrificed and organs (a) lung (b) spleen and (c) liver were plated on arginine and methionine containing plates to measure organ burden. The results are shown in FIGS. 5A to 5C.

Strain Mc$^2$8398 is Highly Attenuated Compared to Other Auxotrophic Strains in Immunocompromised Rag$^{-/-}$ Mice Model.

Rag−/− mice (4/group) were infected intravenously with WT (H37Rv, CDC1551) and auxotrophic strains (mc$^2$8392, mc$^2$8398, mc$^2$7901, mc$^2$7902) at a very high dose of 10$^8$ bacilli/animal. At the indicated time points, animals were sacrificed and organs (a) lung (b) liver and (c) spleen were plated on arginine and methionine containing plates to measure organ burden. The results are shown in FIGS. 6A to 6C.

Strain Mc$^2$8398 has Protective Efficacy Against Wild Type *Mycobacterium tuberculosis* Strain H37Rv by Different Routes of Immunization.

The strains and dosages in the experiment are provided in Table 2. C57BL/6 mice were immunized with PBS, BCG, or mc$^2$8398 subcutaneously (SQ) or intravenously (iv) at Day 0 with 10$^6$ bacilli/mouse and were boosted after 4 weeks with the indicated strains in Table 1, at a dose of 10$^6$ bacilli/mouse. Four weeks following the booster immunization, the mice received a low dose aerosol challenge of ~275 CFU/mouse of strain H37Rv. Organs were harvested at 2, 3, 8, 12, and 24 weeks post-challenge and plated to determine CFU burden in the lungs and spleen. FIG. 7 is an illustration showing the immunization and challenge schedule, and the results are shown in FIGS. 8A and 8B.

TABLE 2

| Group | Immunization ($10^6$) | Booster ($10^6$) | Challenge |
|---|---|---|---|
| 1 | Saline | | H37Rv, aerosol |
| 2 | BCG (SQ) | | H37Rv, aerosol |
| 3 | BCG (SQ) | $mc^2$8398 (SQ) | H37Rv, aerosol |
| 4 | $mc^2$8398(SQ) | | H37Rv, aerosol |
| 5 | $mc^2$8398(SQ) | $mc^2$8398 (SQ) | H37Rv, aerosol |
| 6 | $mc^2$8398 (iv) | | H37Rv, aerosol |

Protective Efficacy of Various Auxotrophic Mutants Against Clinical, Highly Virulent *Mycobacterium tuberculosis* Beijing Strain (HN878).

Figure 9:
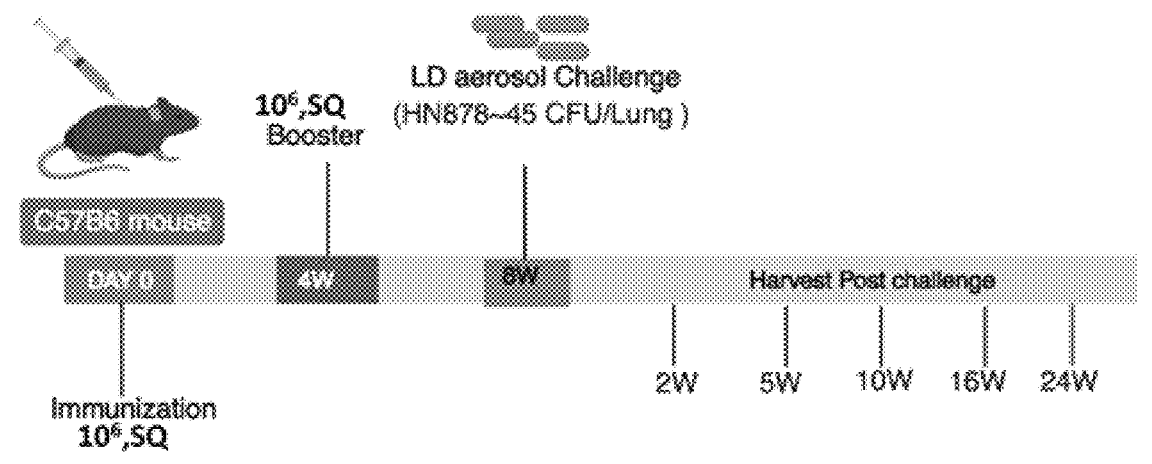

The strains and dosages used are provided in Table 3. C57BL/6 mice are immunized with PBS, BCG, or $mc^2$8398 subcutaneously (SQ) or intravenously (iv) at Day 0 with $10^6$ bacilli/mouse and are boosted after 4 weeks with a same dose ($10^6$ bacilli/mouse) of the same strain. Four weeks following the booster immunization, the mice receive a low dose aerosol challenge of ~45 CFU/mouse of the virulent clinical isolate Beijing strain HN878. At 2, 5, 10, 16, and 24 weeks (W) post-challenge, organs are harvested and plated to determine CFU burden in the lungs and spleen. FIG. 9 is an illustration showing the immunization and challenge schedule.

TABLE 3

| Group | Immunization ($10^6$) | Booster ($10^6$) | Challenge |
|---|---|---|---|
| 1 | Saline | | HN878, aerosol |
| 2 | BCG (SQ) | BCG (SQ) | HN878, aerosol |
| 3 | $mc^2$7901 (SQ) | $mc^2$7901 (SQ) | HN878, aerosol |
| 4 | $mc^2$7902 (SQ) | $mc^2$7902 (SQ) | HN878, aerosol |
| 5 | $mc^2$8392 (SQ) | $mc^2$8392 (SQ) | HN878, aerosol |
| 6 | $mc^2$8398 (SQ) | $mc^2$8398 (SQ) | HN878, aerosol |

Set forth below are some embodiments of the auxotrophic *mycobacterium*, the compositions, and the methods disclosed herein.

Embodiment 1: An auxotrophic *mycobacterium* comprising a mycobacterial genome in which (i) a gene encoding an enzyme essential in an arginine synthesis pathway has been fully or partially deleted and (ii) a gene encoding an enzyme essential in a methionine synthesis pathway has been fully or partially deleted.

Embodiment 2: The auxotrophic *mycobacterium* of Embodiment 1, which is incapable of synthesizing arginine and methionine.

Embodiment 3: The auxotrophic *mycobacterium* of Embodiment 1 or Embodiment 2, wherein the auxotrophic *mycobacterium* prior to the full or partial gene deletions of a gene encoding an enzyme essential in an arginine synthesis pathway and a gene encoding an enzyme essential in a methionine synthesis pathway is a *Mycobacterium tuberculosis*.

Embodiment 4: The auxotrophic *mycobacterium* of Embodiment 1 or Embodiment 2, wherein the auxotrophic *mycobacterium* prior to the full or partial gene deletions of a gene encoding an enzyme essential in an arginine synthesis pathway and a gene encoding an enzyme essential in a methionine synthesis pathway is a *Mycobacterium bovis Bacillus* Calmette-Guérin.

Embodiment 5: The auxotrophic *mycobacterium* of any one of Embodiments 1-4, wherein the gene encoding an enzyme essential in an arginine synthesis pathway is a mycobacterial argB gene or encodes a mycobacterial ArgB enzyme.

Embodiment 6: The auxotrophic *mycobacterium* of any one of Embodiments 1-5, wherein the gene encoding an enzyme essential in a methionine synthesis pathway is a mycobacterial metA gene or encodes a mycobacterial MetA enzyme.

Embodiment 7: The auxotrophic *mycobacterium* of any one of Embodiments 1-6, wherein the auxotrophic *mycobacterium* prior to the full or partial gene deletions of a gene encoding an enzyme essential in an arginine synthesis pathway and a gene encoding an enzyme essential in a methionine synthesis pathway is an H37Rv *Mycobacterium tuberculosis*.

Embodiment 8: A composition comprising the auxotrophic *mycobacterium* of any of Embodiments 1-7 and a carrier.

Embodiment 9: The composition of Embodiment 8 which is a vaccine.

Embodiment 10: The composition of Embodiment 8 or Embodiment 9, wherein the composition does not comprise arginine or methionine.

Embodiment 11: The composition of Embodiment 8 or Embodiment 9, wherein the composition comprises an amount of arginine and an amount of methionine.

Embodiment 12: A method of eliciting an immune response in a subject comprising administering to the subject the composition of any one of Embodiments 8-11 in an amount effective to elicit an immune response.

Embodiment 13: A method of vaccinating a subject comprising administering to the subject the composition of any one of Embodiments 8-11 in an amount effective to vaccinate a subject.

Embodiment 14: A method of treating a subject for tuberculosis comprising administering to the subject the composition of any one of Embodiments 8-11 in an amount effective to treat a subject.

Embodiment 15: The method of any one of Embodiments 12-14, wherein the subject has pulmonary tuberculosis.

Embodiment 16: The method of Embodiment 14, wherein the tuberculosis is pulmonary tuberculosis.

Embodiment 17: The method of any one of Embodiments 12-14, wherein the subject has tuberculosis meningitis.

Embodiment 18: The method of Embodiment 14, wherein the tuberculosis is tuberculosis meningitis.

Embodiment 19: A method of treating a subject for a cancer comprising administering to the subject the composition of any one of Embodiments 8-11 in an amount effective to treat a subject.

Embodiment 20: The method of Embodiment 19, wherein the cancer is a genitourinary cancer.

Embodiment 21: The method of Embodiment 19 or Embodiment 20, wherein the cancer is a non-invasive bladder cancer.

Embodiment 22: The method of Embodiment 21, wherein the amount of the composition is administered into the bladder of the subject via a catheter.

Embodiment 23: The method of any one of Embodiments 19-22, wherein the subject is immunocompromised.

Embodiment 24: The method of any one of Embodiments 12-23, wherein the subject is human.

Embodiment 25: A method of determining the efficacy of a candidate tuberculosis vaccine, comprising: administering the candidate tuberculosis vaccine to an animal which has been infected with the auxotrophic *mycobacterium* of any of Embodiments 1-7, quantifying the amount of the auxotrophic *mycobacterium* in the animal at one or more time points subsequent to administering the candidate tuberculosis vaccine, and comparing the amount of auxotrophic *mycobacterium* quantified to a predetermined control amount, or to the amount of auxotrophic *mycobacterium* infected into the animal, so as to determine the efficacy of the candidate tuberculosis vaccine.

Embodiment 26: A method of determining the efficacy of a candidate small organic molecule tuberculosis treatment, comprising: administering the small organic molecule tuberculosis treatment to an animal which has been infected with the auxotrophic *mycobacterium* of any one of Embodiments 1-7, quantifying the amount of auxotrophic *mycobacterium* in the animal at one or more time points subsequent to administering the candidate tuberculosis vaccine, and comparing the amount of auxotrophic *mycobacterium* quantified to a predetermined control amount, or to the amount of auxotrophic *mycobacterium* infected into the animal, so as to determine the efficacy of the small organic molecule tuberculosis treatment.

Embodiment 27: The method of Embodiment 25 or Embodiment 26, wherein the *mycobacterium* further comprises a reporter gene insertion in the genome thereof and wherein the amount of auxotrophic *mycobacterium* in the animal at one or more time points is quantified by quantifying a reporter signal.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Throughout this application various publications are referred to. Full citations for these references may be found at the end of the specification. The disclosures of these publications, and all patents, patent application publications and books referred to herein, are incorporated herein by reference in their entirety to more fully describe the art to which the subject invention pertains.

One skilled in the art will readily appreciate that the specific methods and results discussed hereinabove are merely illustrative of the invention as described more fully in the claims that follow thereafter.

REFERENCES

1. Berney, M, et al. (2015) Essential roles of methionine and S-adenosylmethionine in the autarkic lifestyle of *Mycobacterium tuberculosis*. Proc Natl Acad Sci USA 112: 10008-10013.
2. Minassian, A M, et al. (2012) A human challenge model for *Mycobacterium tuberculosis* using *Mycobacterium bovis* bacille Calmette-Guerin. *J Infect Dis* 205(7):1035-1042.
3. N Thilothammal, et al. (1996) Does BCG vaccine prevent tuberculous meningitis? *Archives of Disease in Childhood* 74.
4. Alvaro, M (2017) BCG-A throwback from the stone age of vaccines opened the path for bladder cancer immunotherapy. *The Canadian Journal of Urology* 24(3):8788-8793.
5. Gandhi, N M, Morales, A, & Lamm, D L (2013) *Bacillus* Calmette-Guerin immunotherapy for genitourinary cancer. *BJU Int* 112(3):288-297.
6. Ziegler J, et al. (2018) Disseminated *Mycobacterium bovis* infection post-kidney transplant following remote intravesical BCG therapy for bladder cancer. *Transpl Infect Dis*:e12931.
7. Sheron M W, Holt S L, & Ingram C W (2017) *Mycobacterium bovis* Cerebellar Abscess Following Treatment With *Bacillus* Calmette-Guerin. *J Pharm Pract* 30(3): 378-380.
8. Marquez-Batalla S, Fraile-Villarejo E, Belhassen-Garcia M, Gutierrez-Zubiaurre N, & Cordero-Sanchez M (2014) Disseminated infection due to *Mycobacterium bovis* after intravesical BCG instillation. *World J Clin Cases* 2(7): 301-303.
9. Serretta, V. (2015) Although rare, severe complications following intravesical *bacillus* Calmette-Guerin treatment should not be overlooked! *Infect Dis* (Lond) 47(10):732-733.
10. Koya, M P, Simon M A, & Soloway M S (2006) Complications of Intravesical Therapy for Urothelial Cancer of the Bladder. *The Journal of Urology* 175(6): 2004-2010.
11. Jain, P., et al. (2014) Specialized transduction designed for precise high-throughput unmarked deletions in *Mycobacterium tuberculosis*. MBio 5(3):e01245-e14.
12. Tiwari, S. et al, *Arginine-deprivation-induced oxidative damage sterilizes Mycobacterium tuberculosis*, Proc. Natl. Acad. Sci. USA, 2018.
13. Vilchèze, C, et al, (2018). *Rational Design of Biosafety Level 2-Approved, Multidrug Resistant Strains of Mycobacterium tuberculosis through Nutrient Auxotrophy*, mBio 9 (3): e00938-18, pages 1-12.

What is claimed is:

1. An auxotrophic *mycobacterium* comprising a mycobacterial genome in which (i) argB gene, or a gene encoding a mycobacterial ArgB enzyme, has been fully or partially deleted and (ii) metA gene, or a gene encoding a mycobacterial MetA enzyme, has been fully or partially deleted, wherein the mycobacterium is sterilized in the absence of arginine and methionine.

2. The auxotrophic *mycobacterium* of claim 1, which is incapable of synthesizing arginine and methionine.

3. The auxotrophic *mycobacterium* of claim 1, wherein the auxotrophic *mycobacterium* is a *Mycobacterium tuberculosis*.

4. The auxotrophic *mycobacterium* of claim 1, wherein the auxotrophic *mycobacterium* is a *Mycobacterium bovis* Bacillus Calmette-Guérin.

5. The auxotrophic *mycobacterium* of claim 1, wherein the auxotrophic *mycobacterium* is an H37Rv *Mycobacterium tuberculosis*.

6. A composition comprising the auxotrophic *mycobacterium* of claim 1, and a carrier.

7. The composition of claim 6, which is a vaccine.

8. The composition of claim 6, wherein the composition does not comprise arginine or methionine.

9. The composition of claim 6, wherein the composition comprises an amount of arginine and an amount of methionine.

10. A method of eliciting an immune response in a subject comprising administering to the subject the composition of claim 6 in an amount effective to elicit an immune response.

11. A method of vaccinating a subject comprising administering to the subject the composition of claim 6 in an amount effective to vaccinate a subject.

12. A method of treating a subject for tuberculosis comprising administering to the subject the composition of claim 6 in an amount effective to treat a subject.

13. The method of claim 10, wherein the subject has pulmonary tuberculosis.

14. The method of claim 12, wherein the tuberculosis is pulmonary tuberculosis.

15. The method of claim 10, wherein the subject has tuberculosis meningitis.

16. The method of claim 12, wherein the tuberculosis is tuberculosis meningitis.

17. A method of treating a subject for a cancer comprising administering to the subject the composition of claim 6 in an amount effective to treat a subject.

18. The method of claim 17, wherein the cancer is a genitourinary cancer.

19. The method of claim 17, wherein the cancer is a non-invasive bladder cancer.

20. The method of claim 19, wherein the amount of the composition is administered into the bladder of the subject via a catheter.

21. The method of claim 17, wherein the subject is immunocompromised.

22. The method of claim 10, wherein the subject is human.

* * * * *